(12) United States Patent
Mukai et al.

(10) Patent No.: US 8,235,528 B2
(45) Date of Patent: Aug. 7, 2012

(54) FUNDUS PHOTOGRAPHING APPARATUS

(75) Inventors: Hideo Mukai, Toyohashi (JP); Masaaki Hanebuchi, Aichi-ken (JP); Yoshihiko Yamada, Seto (JP)

(73) Assignee: Nidek Co., Ltd., Aichi-ken (JP)

( * ) Notice: Subject to any disclaimer, the term of this patent is extended or adjusted under 35 U.S.C. 154(b) by 0 days.

(21) Appl. No.: 12/771,016

(22) Filed: Apr. 30, 2010

(65) Prior Publication Data
US 2010/0277692 A1 Nov. 4, 2010

(30) Foreign Application Priority Data

Apr. 30, 2009 (JP) ................................. 2009-111455

(51) Int. Cl.
*A61B 3/14* (2006.01)
*A61B 3/10* (2006.01)

(52) U.S. Cl. ......... 351/208; 351/205; 351/206; 351/221
(58) Field of Classification Search .................. 351/208, 351/200, 205–206, 209, 210, 221, 246
See application file for complete search history.

(56) References Cited

U.S. PATENT DOCUMENTS

| | | | | |
|---|---|---|---|---|
| 5,572,266 | A * | 11/1996 | Ohtsuka ........................ | 396/18 |
| 2002/0085173 | A1* | 7/2002 | Schippert et al. ............. | 351/200 |
| 2005/0254008 | A1 | 11/2005 | Ferguson et al. | |
| 2007/0291230 | A1 | 12/2007 | Yamaguchi et al. | |
| 2008/0151189 | A1* | 6/2008 | Iwa et al. ....................... | 351/206 |

FOREIGN PATENT DOCUMENTS

JP 07-171107 7/1995

* cited by examiner

*Primary Examiner* — Dawayne A Pinkney
(74) *Attorney, Agent, or Firm* — Muncy, Geissler, Olds & Lowe, PLLC

(57) ABSTRACT

A fundus photographing apparatus includes a first photographing unit arranged to obtain a first fundus image and including a first illumination optical system including a first light source and a scanning unit, a first photographing optical system and a wavefront compensating unit including a wavefront sensor and a wavefront compensating device, a second photographing unit arranged to obtain a second fundus image of a wide area including a scanning area by the scanning unit and including a second illumination optical system and a second photographing optical system arranged to obtain the second fundus image with a wider view angle under lower magnification than the first fundus image, a monitor, and a control unit arranged to display on the monitor the first and second fundus images, and display an indicator on the second fundus image displayed on the monitor, the indicator indicating a photographed portion of the first fundus image.

7 Claims, 4 Drawing Sheets

FUNDUS PHOTOGRAPHING APPARATUS

BACKGROUND OF THE INVENTION

1. Field of the Invention

The present invention relates to a fundus photographing apparatus for making fundus observation and fundus photographing by scanning a fundus of an examinee's eye with illumination light such as laser light.

2. Description of Related Art

Conventionally, for an ophthalmic photographing apparatus, there is known a fundus photographing apparatus for obtaining a fundus image by two-dimensionally scanning a fundus of an examinee's eye with a spot of laser light and photo-receiving the laser light reflected from the fundus (i.e., a scanning laser ophthalmoscope). For example, the fundus photographing apparatus having the configuration described above is arranged to two-dimensionally scan the fundus with the laser light by the combined use of a polygon mirror and a galvano mirror (see Japanese Patent Application Unexamined Publication No. Hei07-171107).

However, while the fundus photographing apparatus described above is capable of photographing a front image of the fundus at high resolution, a technique has recently been desired that enables obtainment of a fundus image at higher resolution under high magnification, and thus achieves fundus observation at a cell level.

SUMMARY OF THE INVENTION

An object of the invention is to overcome the problem described above and to provide a fundus photographing apparatus which is capable of efficiently obtaining an image of a fundus at higher resolution, with which fundus observation at a cell level is achieved.

To achieve the objects and in accordance with the purpose of the present invention, a fundus photographing apparatus for photographing a fundus of an examinee's eye includes a first photographing unit arranged to obtain a first fundus image and including a first illumination optical system arranged to project illumination light to the fundus and including a first light source arranged to emit the illumination light and a scanning unit arranged to two-dimensionally scan the illumination light on the fundus, a first photographing optical system including a first photo-receiving element arranged to photo-receive the illumination light reflected from the fundus and obtain the first fundus image and a wave front compensating unit including a wavefront sensor arranged to photo-receive light reflected from the eye and detect wavefront aberration of the eye and a wavefront compensating device disposed on an optical path of the first photographing optical system and arranged to compensate the wavefront aberration based on a detection result by the wavefront sensor, a second photographing unit arranged to obtain a second fundus image of a wide area that includes a scanning area by the scanning unit of the first illumination optical system and including a second illumination optical system including a second light source arranged to emit illumination light and arranged to project the illumination light to the fundus and a second photographing optical system including a second photo-receiving element arranged to photo-receive the illumination light reflected from the fundus and obtain the second fundus image with a view angle wider than the first fundus image under magnification lower than the first fundus image, a monitor, and a control unit arranged to display on the monitor the first fundus image and the second fundus image, and display an indicator on the second fundus image displayed on the monitor, the indicator indicating a photographed portion of the first fundus image.

Additional objects and advantages of the invention are set forth in the description which follows, are obvious from the description, or may be learned by practicing the invention. The objects and advantages of the invention may be realized and attained by the fundus photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
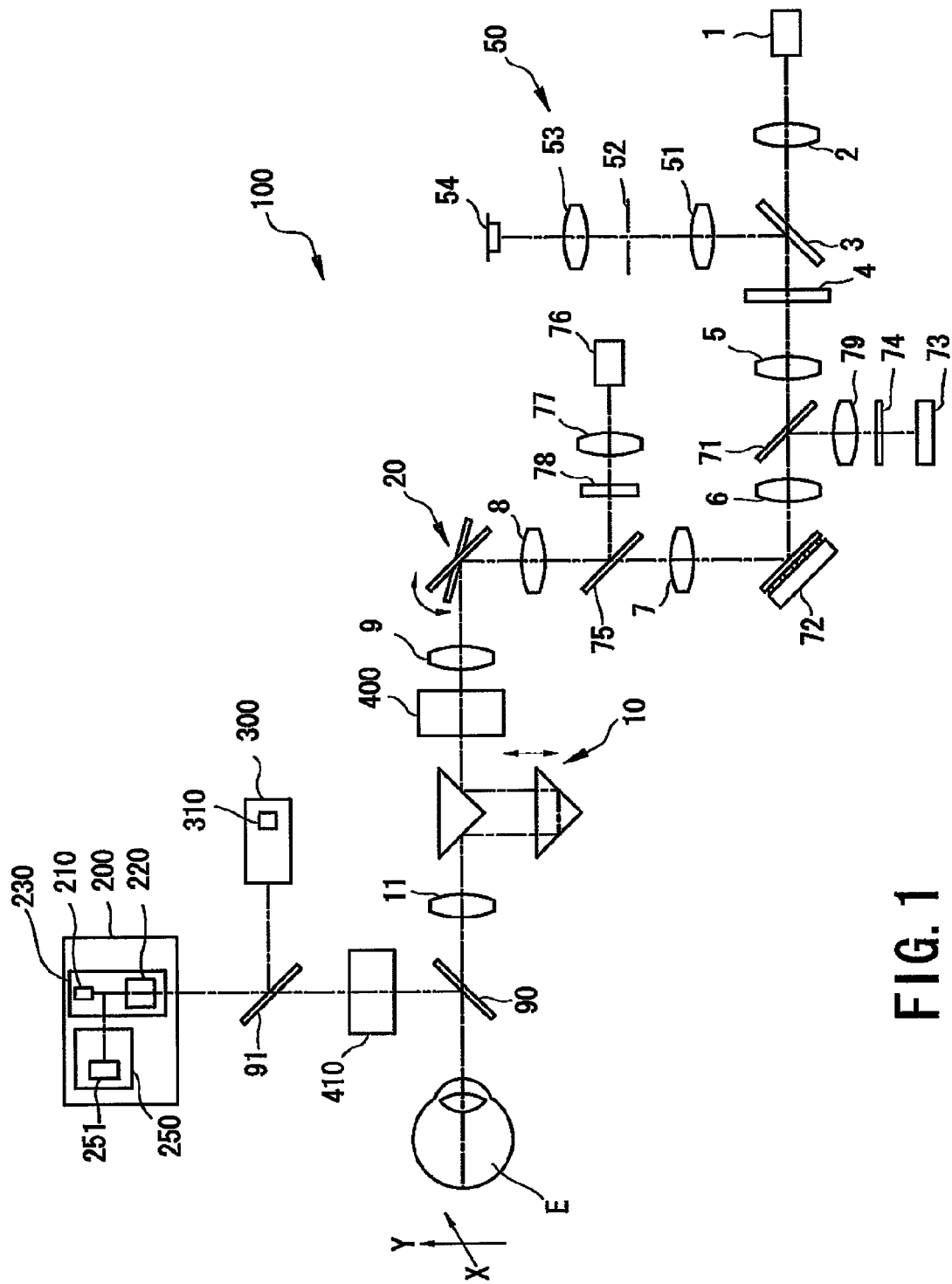
FIG. 1 is a schematic view of an optical system of a fundus photographing apparatus according to a preferred embodiment of the present invention.

A description of a fundus photographing apparatus according to a preferred embodiment of the present invention is provided below with reference to the accompanying drawings. FIG. 1 is a schematic view of an optical system of a fundus photographing apparatus according to the preferred embodiment of the present invention. The fundus photographing apparatus according to the preferred embodiment of the present invention is roughly constituted of a first photographing unit 100 arranged to photograph (obtain an image of) a fundus of an examinee's eye E at higher resolution under high magnification, a second photographing unit 200 arranged to obtain an image for fundus observation (hereinafter, referred to as a second fundus image) used for specifying a portion of the fundus photographed (the fundus image obtained) by the first photographing unit 100 (hereinafter, referred to as a first fundus image), and a tracking unit (position detecting unit) 300 arranged to detect a time-varying change in positional deviation caused by involuntary fine movement of the eye E being subjected to photographing and obtain information on the movement position of the eye E. The first photographing unit 100 includes a wave front compensating unit arranged to compensate low-order aberration and high-order aberration of the eye E. The first photographing unit 100 has a view angle that is made narrower than the second photographing unit 200 in order to magnify and observe the fundus (a narrow view angle), and the second photographing unit 200 has a view angle such that a wide area of the fundus can be observed in order to find the portion of the fundus at which the first fundus image is photographed (a wide view angle).

The first photographing unit 100 includes a first illumination optical system arranged to project illumination light (an illuminating light bundle) to the eye E and two-dimensionally scan the fundus with the illumination light, a first photographing optical system 50 arranged to photo-receive the illumination light reflected from the fundus and obtain the first fundus image, and the wavefront compensating unit arranged to detect and compensate wave front aberration of the eye E. The first photographing unit 100 has a configuration of a scanning laser ophthalmoscope (SLO) that includes a confocal optical system.

The first illumination optical system includes a light source 1 (a first light source) arranged to emit the illumination light to illuminate the fundus with the illumination light (to project the illumination light to the fundus), and a scanning unit 20 arranged to two-dimensionally scan the illumination light (spot light) on the fundus. The illumination light emitted from the light source 1 is illumination light within a near infrared wavelength range that is difficult to be visually perceived by the examinee's eye. In the preferred embodiment of the present invention, an SLD (Super Luminescent Diode) light source arranged to emit light with a wavelength of 840 nm is used as the light source 1. With the use of the SLD as the light source, speckle noise of the reflection light at the fundus can be reduced compared with a case where a light source arranged to emit laser light is used as the light source. It is to be noted that the light source may be any light source if it emits spot light having a property of strong convergence, and to be specific, it may be a semiconductor laser.

First, a description of the first illumination optical system will be provided. The first illumination optical system includes a lens 2, a beam splitter 3, a polarizing plate 4, a lens 5, a beam splitter 71, a lens 6, a wavefront compensating device 72, a lens 7, and a beam splitter 75, which are disposed on an optical path from the light source 1 to the fundus. The first illumination optical system further includes a lens 8, the scanning unit 20 arranged to two-dimensionally scan the illumination light on the fundus, a lens 9, a deflecting unit 400 arranged to correct a scanning position of the two-dimensionally scanned illumination light, a vision correcting unit 10 including two prisms, a lens 11, and a beam splitter 90 arranged to make optical axes of the second photographing unit 200 and other units almost coaxial with the optical axis of the first illumination optical system. In the preferred embodiment of the present invention, a half mirror is used as the beam splitter 3.

The illumination light emitted from the light source 1 is made into parallel light by the lens 2 and passes through the beam splitter 3, and then the illumination light is made to have only an s-polarized component by the polarizing plate 4 in the preferred embodiment of the present invention. The illumination light after passing through the polarizing plate 4 is once collected by the lens 5, passes through the beam splitter 71, is made into parallel light by the lens 6, and enters the wavefront compensating device 72. The illumination light reflected by the wavefront compensating device 72 is relayed via the lens 7 and the lens 8, and heads for the scanning unit 20.

The scanning unit 20 is arranged to two-dimensionally scan the illumination light on the fundus. To be specific, the scanning of the illumination light on the fundus is performed in X- and Y-directions as shown in FIG. 1. The scanning unit 20 includes a mirror (resonant mirror) that functions as a deflection member arranged to deflect the illumination light in a horizontal direction (X-direction) to scan on the fundus, a mirror (galvano mirror) that functions as a deflection member arranged to deflect the illumination light in a vertical direction (Y-direction) that is vertical to the scanning direction of the horizontal direction to scan on the fundus, and driving units arranged to drive the mirrors, in the preferred embodiment of the present invention. The illumination light after passing through the scanning unit 20 is collected again by the lens 9. The deflecting unit 400 is arranged to deflect the illumination light via the scanning unit 20 by a predetermined amount further in the horizontal or vertical direction, and includes two galvano mirrors in the preferred embodiment of the present invention. The illumination light after passing through the deflecting unit 400 passes through the vision correcting unit 10, the lens 11 and the beam splitter 90, and is collected on the fundus. The collected illumination light is two-dimensionally scanned on the fundus by the scanning unit 20. The vision correcting unit 10 is capable of varying its optical path length by moving one of the prisms in the arrow directions shown in FIG. 1. The beam splitter 90 is a dichroic mirror, and has a property of reflecting the light from the second photographing unit 200 and the light from the tracking unit 300 and transmitting the light from the light source 1 and the light from a light source 76 to be described later. Exit ends of the light source 1 and the light source 76 are made coaxial with the fundus. Described above is the configuration of the first illumination optical system arranged to two-dimensionally illuminate the eye E with illumination light.

Next, a description of the first photographing optical system 50 will be provided. The first photographing optical system 50 shares the optical path from the beam splitter 90 to the beam splitter 3 with the first illumination optical system, and further includes a lens 51, a pinhole plate 52, a condenser lens 53, and a photodetector 54. The pinhole plate 52 has a pinhole that is made coaxial with the fundus. The photodetector 54 includes an APD (Avalanche Photodiode).

The illumination light emitted from the light source 1 and reflected from the fundus travels on the optical path in the reverse direction to the polarizing plate 4, and only the light having the s-polarized component is transmitted by the polarizing plate 4, and thereafter, a part of the light is reflected by the beam splitter 3. The reflection light comes into focus on the pinhole of the pinhole plate 52 via the lens 51. The light in focus on the pinhole is photo-received on the photodetector 54 via the lens 53. While a part of the illumination light is reflected from a cornea of the eye, a large part of the corneal reflection light is removed by the pinhole plate 52, so that the corneal reflection light has a reduced adverse effect on the obtained image. Thus, the photodetector 54 is capable of photo-receiving the reflection light from the fundus while reducing an adverse effect of the corneal reflection light. The beam splitter 3 may be a hole mirror. In the case of using a hole mirror, the hole of the hole mirror prevents the corneal reflection light from entering the first photographing optical system 50.

Described above is the configuration of the first photographing optical system 50. The image that is obtained by photo-receiving the light by the first photographing optical system 50 and subjected to image processing defines the first fundus image. Angles at which the mirrors of the scanning unit 20 are swung (swing angles) are set such that a fundus image with a given view angle is obtained by the first photographing unit 100. The view angle is set such that a predetermined area of the fundus is observed and photographed under high magnification (e.g., observed and photographed at a cell level). The view angle is preferably about 1 to 5 degrees, and in the preferred embodiment of the present invention, 1.5 degrees. A photographed area of the first fundus image is about 500 µm square, which depends on the visibility of an examinee's eye or other factors.

A description of the wavefront compensating unit (compensating optical system) will be provided. Sharing a part of the optical path with the first illumination optical system, some optical elements of the wavefront compensating unit are disposed on the optical path of the first illumination optical system. The wavefront compensating unit includes a wavefront sensor 73, a polarizing plate 74, the light source 76, a lens 77, a polarizing plate 78 and a lens 79. The wavefront compensating unit shares the optical members from the beam splitter 71 to the beam splitter 90 disposed on the optical path of the first illumination optical system with the first illumination optical system. The wavefront sensor 73 includes a microlens array including numbers of microlenses, and a two-dimensional photodetector arranged to photo-receive the light transmitted by the microlens array. The light source 76 that defines a light source for aberration detection (a third light source) is preferably a laser diode arranged to emit laser light with a wavelength of 780 nm within an infrared wavelength range that is different from the laser light emitted from the light source 1. The laser light emitted from the light source 76 is made into parallel light by the lens 77, made into polarized light (p-polarized light) by the polarizing plate 78 so as to have a polarization direction perpendicular to the polarization direction of the illumination light emitted from the first light source 1, and directed to the optical path of the first illumination optical system by the beam splitter 75. A half mirror is used as the beam splitter 75. The polarizing plate 78 defines a first polarizing unit of the wavefront compensating unit, which is arranged to polarize the light that is emitted from the third light source and projected to the fundus such that the light has the given polarization direction.

The laser light reflected by the beam splitter 75 is collected on the fundus of the eye E via the optical path of the first illumination optical system. The laser light reflected from the fundus is reflected by the wavefront compensating device 72 via the optical elements of the first illumination optical system, reflected to deviate from the optical path of the first illumination optical system by the beam splitter 71, and then directed to the wavefront sensor 73 via the lens 79 and the polarizing plate 74 arranged to transmit the light having the s-polarized component. The polarizing plate 74 defines a second polarizing unit of the wavefront compensating unit, which is arranged to cut off the light having the polarization direction that is emitted from the third light source (i.e., the p-polarized light), and transmit the light having the polarization direction perpendicular to the polarization direction of the p-polarized light (i.e., the s-polarized light) and guide to the wavefront sensor 73. The beam splitter 71 has a property of transmitting the light from the light source 1 (light with a wavelength of 840 nm) and reflecting the light from the light source 76 for aberration detection (light with a wavelength of 780 nm). The wavefront sensor 73 is arranged to detect the light having the s-polarized component among the scattered laser light from the fundus. Thus, the light reflected from the cornea and the light reflected by the optical elements are prevented from being detected by the wavefront sensor 73. The scanning unit 20, the reflection surface of the wavefront compensating device 72, and the microlens array of the wavefront sensor 73 are made almost coaxial with a pupil of the eye E. A photo-receiving surface of the wavefront sensor 73 is made almost coaxial with the fundus of the eye E. The wavefront sensor 73 includes an element capable of detecting wavefront aberration such as low-order aberration and high-order aberration, examples of such an element including a Shack-Hartmann sensor, and a wavefront curvature sensor for detecting change in light intensity.

The wavefront compensating device 72 may be a liquid-crystal spatial phase modulator using preferably reflective LCOS (Liquid Crystal On Silicon). The wavefront compensating device 72 is disposed in an orientation such that it can compensate wave front aberration of predetermined linear polarization (s-polarization) of the illumination light from the light source 1 (s-polarized light), the illumination light reflected from the fundus (s-polarized light), and the reflection light of the light for wavefront aberration detection (s-polarized light). Having such a configuration, the wavefront compensating device 72 is capable of modulating the light having the s-polarized component among the light entering the wave front compensating device 72. The wavefront compensating device 72 includes a liquid crystal layer having a configuration such that the direction in which liquid crystal molecules are aligned is made almost parallel to a polarization plane of the reflection light entering the wavefront compensating device 72. To be specific, the wavefront compensating device 72 is disposed such that a predetermined plane rotated in accordance with the change in voltage applied to the liquid crystal layer is almost parallel to a plane that includes the axes of the light entering and reflecting from the wave front compensating device 72, and the normal to a mirror layer of the wavefront compensating device 72.

Thus, in the wavefront compensating unit (compensating optical system), the wavefront compensating device 72 is controlled, based on the wavefront aberration of the fundus reflection light of the light source 76 that is detected by the wavefront sensor 73, to remove the wavefront aberration of the illumination light emitted from the light source 1 and the wavefront aberration of the reflection light of the illumination light emitted from the light source 1 in addition to the s-polarized component in the reflection light of the light source 76. In this manner, the wavefront aberration of the illumination light emitted from the light source 1 and the wavefront aberration of the reflection light of the illumination light emitted from the light source 1 are removed, in other words, the first fundus image at high resolution is obtained in which the wavefront aberration of the eye E is removed (the wavefront aberration is compensated). In spite of being a fundus image with a narrow view angle, the obtained first fundus image is a greatly magnified fundus image of higher resolution with which fundus observation at a cell level can be achieved because the scanning of the illumination light is performed on the fundus so that the first fundus image to be obtained is comparable to a conventional fundus image with a wide view angle with respect to the number of pixels necessary to constitute one image, and further the wavefront aberration is compensated. The fundus image obtained by the first photographing unit 100 is stored as the first fundus image in a memory unit.

A description of the second photographing unit 200 will be provided. The second photographing unit 200 is arranged to obtain a fundus image with a view angle wider than the view angle of the first photographing unit 100 (i.e., the second fundus image). The obtained second fundus image is used to specify and find the photographed portion of the fundus at which the first fundus image with the narrow view angle is obtained. It is essential only that the second photographing unit 200 should be capable of obtaining a fundus image with a wide view angle in real time so as to be used as a fundus image for observation. An observation and photographing system used in an already available fundus camera, or an optical system and a control system used in an already available scanning laser ophthalmoscope (SLO) can be used for the second photographing unit 200. Hereinafter, for the sake of simplifying the explanation, a block diagram of the optical systems is shown in FIG. 1.

The second photographing unit 200 includes a second illumination optical system 230 and a second photographing optical system 250. The second illumination optical system 230 includes a second light source 210 arranged to emit illumination light to illuminate the fundus and a scanning unit 220 arranged to two-dimensionally scan the illumination light on the fundus, and is arranged to two-dimensionally illuminate the fundus. The second photographing optical system 250 includes a photodetector 251 arranged to photo-receive the illumination light by the second illumination optical system 230 that is reflected from the fundus, and is arranged to photograph an image of the fundus.

The optical axis of the second photographing unit 200 is made almost coaxial with the optical axis of the first photographing unit 100 by the beam splitter 90 disposed between the scanning unit 20 and the examinee's eye. The optical axis of the second photographing unit 200 is made coaxial with the optical axis of the first photographing unit 100 in front of the examinee's eye. The angle of the beam splitter 90 is set such that reflection light from the cornea that enters the second photographing unit 200 is reduced. The beam splitter 90 has the property of transmitting the light from the light source 1 and the light from the light source 76, and reflecting the light from the second light source 210 and the light from a light source of the tracking unit 300 to be described later. A beam splitter 91 arranged to make the optical axis of the second photographing unit 200 coaxial with the optical axis of the tracking unit 300, and a deflecting unit 410 having the same function as the deflecting unit 400 are disposed on an optical path between the beam splitter 90 and the second photographing unit 200.

The second light source 210 is arranged to emit light within an infrared wavelength range, and a laser diode arranged to emit laser light with a wavelength of 910 nm is preferably used as the second light source 210. The scanning unit 220 includes mirrors arranged to deflect (reflect) the laser light in the X-, and Y-directions as described above. Angles at which the mirrors of the scanning unit 220 are swung (swing angles) are set such that a fundus image with a view angle wider than the view angle of the first photographing unit 100 is obtained by the second photographing unit 200. The view angle is set such that a wide area of the fundus is photographed in order to obtain a characterizing portion of the fundus, to be specific, an area such that a macular spot and a papilla of the fundus are photographed at a time. The view angle is preferably about 20 to 60 degrees, and in the preferred embodiment of the present invention, 35 degrees.

The laser light emitted from the second light source 210 is emitted from the second photographing unit 200 via the second illumination optical system 230. The laser light passes through the beam splitter 91 and the deflecting unit 410, is reflected by the beam splitter 90, and collected on the fundus of the eye E. The laser light reaching the fundus is two-dimensionally scanned on a wide area of the fundus by driving of the scanning unit 220. The reflection light travels on the optical path in the reverse direction, and is photo-received on the photodetector 251 of the second photographing optical system 250. Based on a photo-receiving result obtained by the photodetector 251, the fundus image with the wide view angle (second fundus image) is obtained. Described above is the configuration of the second photographing unit 200. The fundus image obtained by the second photographing unit 200 is stored as the second fundus image in the memory unit 81.

In the preferred embodiment of the present invention, the illumination is performed such that the fundus is two-dimensionally scanned with the use of the scanning unit 220 via the second illumination optical system 230; however, the present invention is not limited hereto. It is also preferable that slit light in a line shape is scanned in a direction perpendicular to the direction of the slit light line, or that an illumination optical system of an already available fundus camera including a hole mirror is used.

A description of the tracking unit 300 will be provided. Usually, an eye finely moves involuntarily even if the eye is fixated, and thus the eye continually moves (finely). Such fine movement of the eye little impairs observation of a wide area of the fundus; however, it impairs observation when a narrow area of the fundus is photographed under high magnification to be observed at a cell level as in the case of the preferred embodiment of the present invention. For this reason, the tracking unit 300 is arranged to detect swinging of the eye caused by involuntary fine movement of the eye or other factors, and obtain information on positional correction (information on a movement position of the eye) that is used for preventing a positional deviation in the first fundus image. The tracking unit 300 includes a light source 310 arranged to emit illumination light within an infrared wavelength range. For example, the light source 310 defines an SLD light source arranged to emit light with a wavelength of 1,060 nm, the tracking unit 300 is arranged to circularly scan the illumination light on the fundus by driving of a resonant mirror to form a tracking indicator having a ring shape, and photo-receive the tracking indicator on a photodetector. The tracking indicator formed on the fundus of the eye E has a ring shape same or a bit smaller in size than the papilla. The illumination light is circularly scanned about 100 to 2,000 times per second by the fast driving of the resonant mirror. The illumination light emitted from the tracking unit 300 is made almost coaxial with the optical axis of the second photographing unit 200 by the beam splitter 91, and then made almost coaxial with the optical axis of the first photographing unit 100 by the beam splitter 90 via the deflecting unit 410. It is to be noted that the beam splitter 91 has a property of reflecting the light from the light source 310, and transmitting the light from the light source 210.

Figure 2:
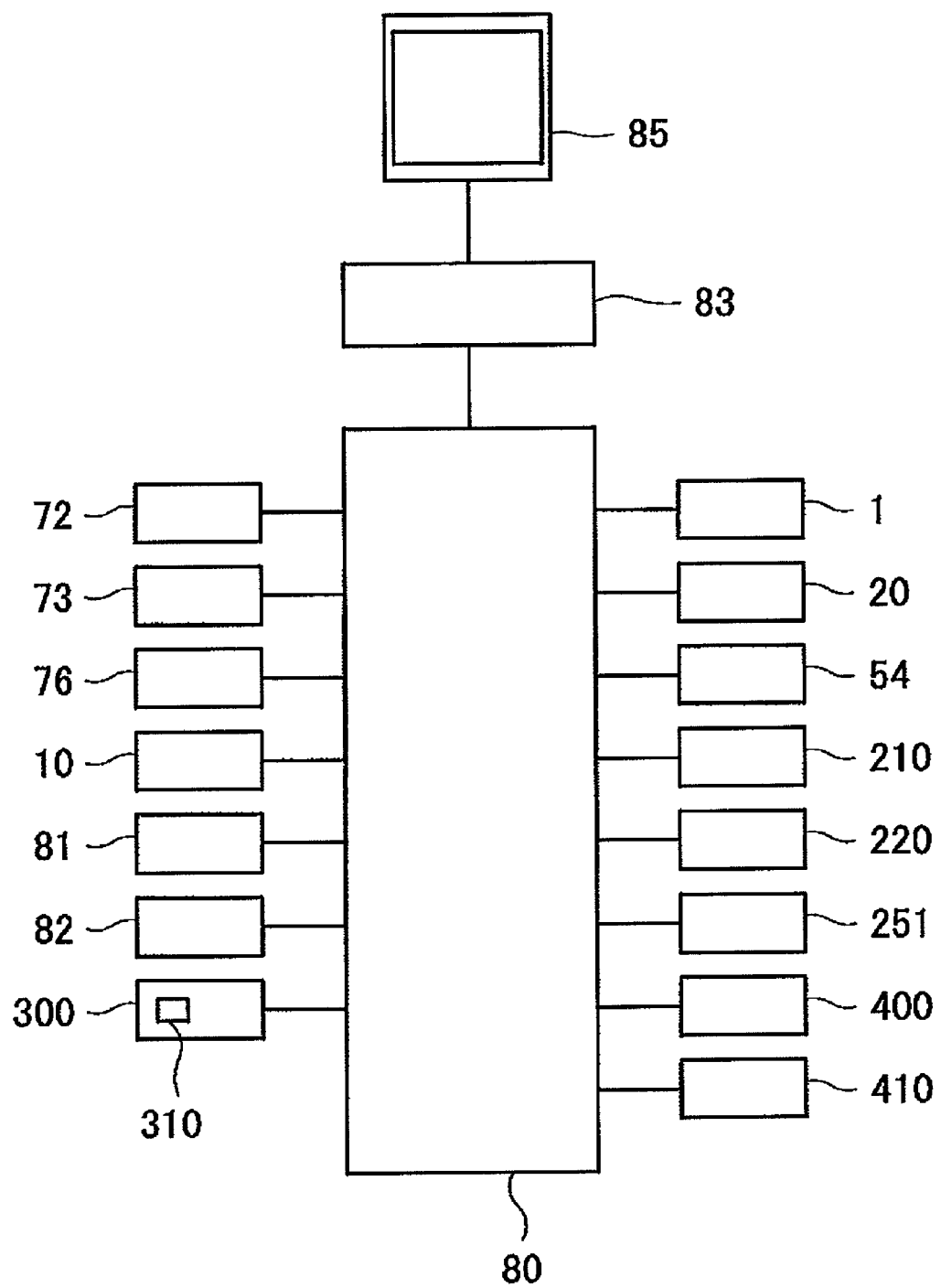
FIG. 2 is a block diagram of a control system.

A description of a control system of the fundus photographing apparatus will be provided. FIG. 2 is a block diagram of the control system of the fundus photographing apparatus according to the preferred embodiment of the present invention. A control unit 80 arranged to perform the control of the entire apparatus is connected with the light source 1, the scanning unit 20, the photodetector 54, the wavefront compensating device 72, the wavefront sensor 73, the light source 76, the light source 210, the scanning unit 220, the photodetector 251, the tracking unit 300, the deflecting unit 400, the deflecting unit 410, the vision correcting unit 10, the memory unit 81, a control unit 82, an image processing unit 83 and a monitor 85. The image processing unit 83 performs display control of the monitor 85 based on photo-receiving signals from the photodetector 54 and the photodetector 251, and thereby images of the examinee's fundus with different view angles, to be specific, the first fundus image and the second fundus image, are displayed on the monitor 85. The memory unit 81 is arranged to store various setting information and photographed images. The monitor 85 is arranged to display the fundus images (first and second fundus images) that are renewed at a given frame rate. The frame rate is preferably 10 to 100 Hz. Thus, the fundus images are displayed as moving images. The control unit 80 functions also as a display control unit of the monitor 85, driving control units of the deflecting units 400 and 410, and emission control units of the light sources 1 and 76 and other elements.

The control unit 80 controls the light source 1 to emit the illumination light based on a signal from the wavefront sensor 73. To be specific, the illumination light emitted from the light source 76 and reflected from the fundus is photo-received on the wavefront sensor 73, and its photo-receiving result is sent to the control unit 80. Based on the wavefront aberration of the fundus reflection light, the control unit 80 drives the wavefront compensating device 72 to remove the wavefront aberration of the examinee's eye. Based on a result of the removal of the wavefront aberration of the fundus reflection light (i.e., a compensation result), the control unit 80 controls the light source 1 to emit the illumination light. A given threshold value is used as the criterion for judging the compensation result, and the result is subjected to processing using the criterion. Thus, since the illumination light from the light source 1 is not projected to the eye E before the wavefront aberration of the eye E is compensated, a first fundus image not appropriate for observation and photographing is never generated. Hence, unnecessary emission of the illumination light from the light source 1 can be eliminated, preventing the eye E from being exposed to useless illumination light. In addition, the amount of electricity consumed by the light source 1 can be reduced.

It is also preferable that in order not to let unnecessary illumination light enter the examinee's eye, the control unit 80 controls the light source 1 and the light source 76 not to emit the illumination light during the time when an alignment state of the second fundus image is not suitable. For example, the control unit 80 may judge the alignment state by a criterion defined by a focus state of the second fundus image (an alignment state in a Z-direction with respect to the fundus). It is also preferable that the control unit 80 controls the light source 310 of the tracking unit 300 to emit the illumination light based on the alignment state of the second fundus image. In the preferred embodiment of the present invention, alignment of the apparatus is performed by photographing an image of an anterior segment of the examinee's eye with the use of the second photographing unit 200 and displaying the image on the monitor 85.

Figure 3:
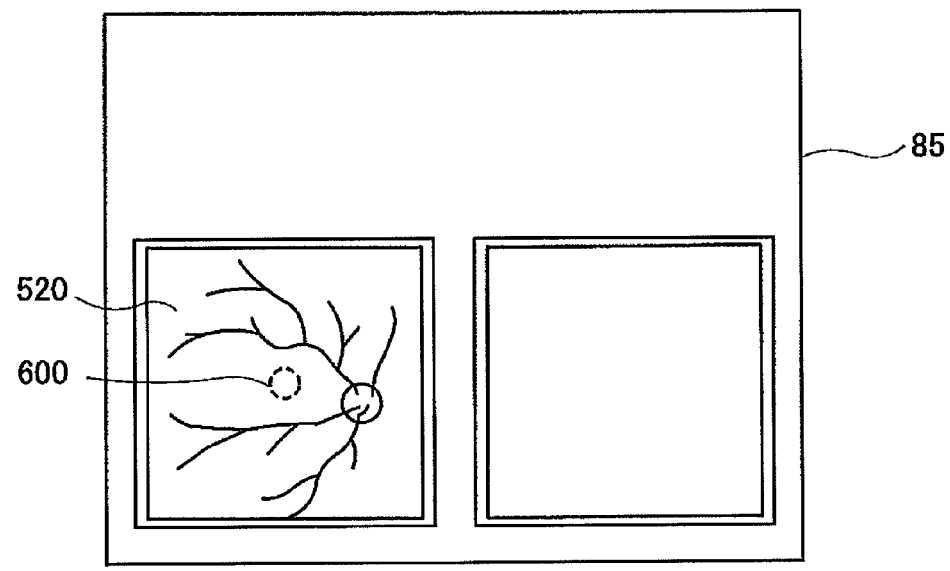
FIG. 3 is a view for illustrating display on a monitor.

Descriptions of operations of the fundus photographing apparatus having the configuration described above will be provided. FIG. 3 is a schematic view for illustrating the display on the monitor 85. An examiner instructs the examinee to fixate his/her eye E to a fixation lamp (not shown), and performs alignment of the apparatus with the eye E with the use of a joystick or other devices (not shown). During the alignment, the vision correcting unit 10 is driven through operation of the control unit 82, and the vision of the eye E is corrected. During the alignment, a second fundus image 520 obtained by the second photographing unit 200 is displayed in a predetermined observation region on the monitor 85, and the examiner completes the alignment, watching the image for observation (second fundus image 520) displayed in the observation region on the monitor 85. Upon completion of the alignment, the examiner inputs a command signal to actuate the tracking unit 300 by means of the control unit 82. Receiving the command signal, the control unit 80 controls the tracking unit 300 to emit the laser light and form the tracking indicator on the fundus of the eye E. At the same time, the control unit 80 controls the monitor 85 to display a reticle mark 600 having the same shape as the tracking indicator at a position on the second fundus image 520 (in the observation region) that corresponds to the position on the fundus where the tracking indicator is formed. Watching the reticle mark 600 formed on the second fundus image 520, the examiner moves the apparatus and the fixation lamp as appropriate to perform alignment thereof such that the papilla of the eye E shown in the observation region is superimposed on the reticle 600.

When the reticle 600 displayed in the observation region and the papilla in the second fundus image 520 are superimposed, the examiner sends a command signal to start tracking to the control unit 80 by means of the control unit 82. Receiving the command signal to start tracking, the control unit 80 drives the tracking unit 300, the deflecting unit 400 and the deflecting unit 410, and starts the tracking of the eye E.

Figure 4A:
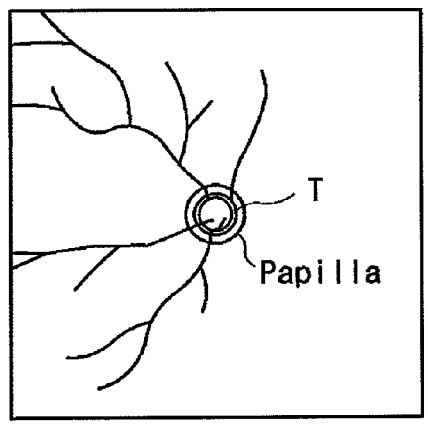
FIGS. 4A and 4B are schematic views showing a state where a tracking indicator is superimposed on a papilla of a fundus.
Figure 4B:
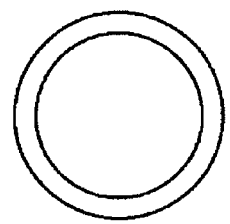
Figure 5A:
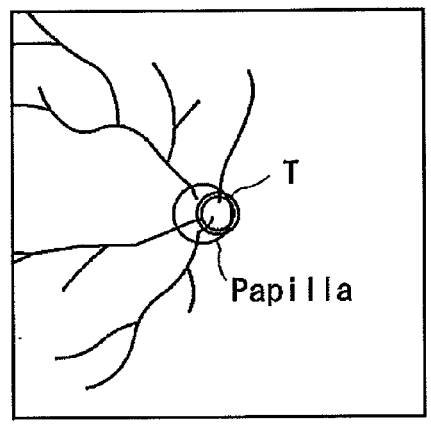
FIGS. 5A and 5B are schematic views showing a state where the tracking indicator is deviated from the papilla of the fundus.
Figure 5B:
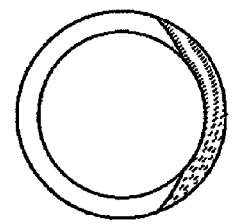

FIGS. 4A and 4B and FIGS. 5A and 5B are schematic views for illustrating a manner of the tracking. FIG. 4A is the schematic view for illustrating a state where the papilla in the second fundus image 520 and the reticle 600 are superimposed, and a tracking indicator T is superimposed on the papilla of the fundus. FIG. 5A is the schematic view for illustrating a state similar to the state shown in FIG. 4A, but the tracking indicator T is deviated from the papilla of the fundus. FIGS. 4B and 5B are the schematic views showing luminance distribution of the tracking indicator T in the state shown in FIG. 4A, and luminance distribution of the tracking indicator T in the state shown in FIG. 5A, respectively.

Shown in FIG. 4A is the state where the eye E does not move after the tracking is started. If the eye E involuntarily moves finely, the papilla is deviated from the tracking indicator T as shown in FIG. 5A. Reflection light of the tracking indicator T in the state of being superimposed completely on the papilla is photo-received on the photodetector of the tracking unit 300 while the overall reflection light has a high luminance as shown in FIG. 4B. Meanwhile, when the papilla is deviated from the tracking indicator T, and a portion of the tracking indicator T is not superimposed on the papilla, a portion of the reflection light corresponding to the portion of the tracking indicator T that is not superimposed has a low luminance as shown in FIG. 5B.

The tracking unit 300 sends in advance to the control unit 80 a photo-receiving result obtained at the start of the tracking as information of criterion, and thereafter sends to the control unit 80 a photo-receiving result (photo-receiving information) at every scanning (every time a ring is formed by scanning) in succession. The control unit 80 compares the photo-receiving information obtained after the start of the tracking with the criterion information, and finds information on the movement position of the eye E using an arithmetical operation in order to obtain photo-receiving information that is the same as the criterion information, in other words, in order to superimpose the entire tracking indicator T on the papilla. Based on the obtained movement position information, the control unit 80 drives the deflecting unit 410. The control unit 80 drives also the deflecting unit 400 in synchronization with the deflecting unit 410.

The tracking as described above allows the deflecting unit 400 and the deflecting unit 410 to be driven such that even if the eye E involuntarily moves finely, such movement of the eye E is compensated, and thus the fundus images displayed on the monitor 85 are prevented from moving.

After the start of the tracking, the control unit 80 drives the light source 76, the scanning unit 20, the wavefront compensating device 72 and the wavefront sensor 73 to compensate the wavefront aberration of the examinee's eye.

Based on a result obtained from optical distribution (a photo-receiving signal) detected by the wavefront sensor 73, the control unit 80 dynamically controls the compensating optical system. For example, in the preferred embodiment of the present invention, the control is performed such that the direction in which the liquid crystal molecules in the liquid crystal panel (liquid crystal layer) of the wavefront compensating device 72 are aligned is changed by voltage control such that a diffraction image of the reflection light from the fundus has the smallest spread width, and phase distribution is controlled.

Upon completion of the compensation of the wavefront aberration, the photographing of the first fundus image is started. Based on the signal (photo-receiving result) from the wavefront sensor 73, the control unit 80 drives the light source 1 and the photodetector 51. The illumination light emitted from the light source 1 is made into the s-polarized light by the polarizing plate 4 and modulated by the wavefront compensating device 72. Then, the illumination light projected to the examinee's eye is two-dimensionally scanned by the scanning unit 20, and collected on the fundus.

The illumination light collected on and reflected from the fundus travels on the optical path in the reverse direction via the scanning unit 20, is modulated by the wavefront compensating device 72, passes through the polarizing plate 4, and then is reflected (deflected) by the beam splitter 3 to be directed to the first photographing optical system 50. The reflection light is collected on the pinhole of the pinhole plate 52 by the lens 51, and is made to enter the photodetector 54 by the lens 53. Based on the photo-receiving signal from the photodetector 54, the image processing unit 83 displays the second fundus image 520 and the first fundus image 530 on the monitor 85 in a comparable manner.

Figure 6A:
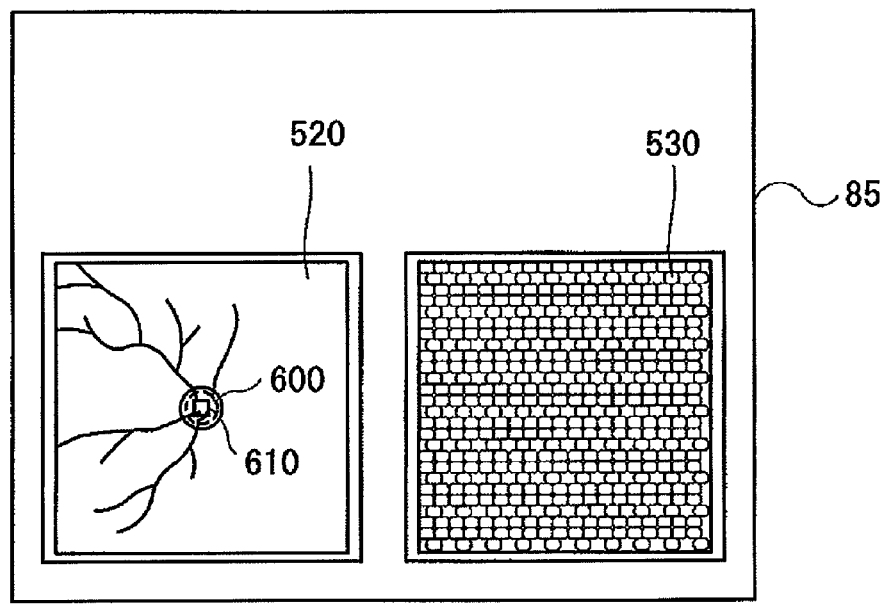
FIGS. 6A and 6B are views for illustrating display on the monitor.
Figure 6B:
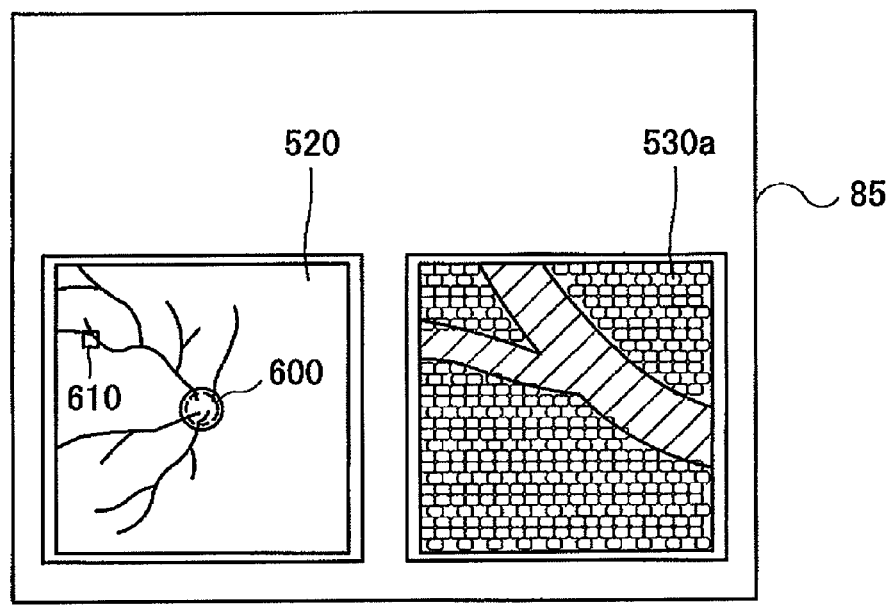

FIGS. 6A and 6B are views showing a state where the first fundus image 530 and the second fundus image 520 are displayed in the respective observation regions on the monitor 85. The second fundus image 520 defines an observation image of the wide area of the fundus. Meanwhile, the first fundus image 530 defines a greatly magnified moving image with a narrow view angle with which fundus observation at a cell level can be achieved. It is to be noted that in the initial state, displayed is the first fundus image 530 of a given area of the fundus with a given view angle (1.5 degrees in the preferred embodiment of the present invention) having an optical axis of the first photographing unit (the main optical axis) as its center (see FIG. 6A). In this initial state, a mark 610 is displayed at a position on the second fundus image 520 (in the observation region), the position corresponding to a photographed portion of the first fundus image 530, and thus the first fundus image 530 is recognizable as a magnified image of which portion of the second fundus image 520.

If observation of a different region (photographed portion) of the second fundus image 520 is to be performed, the mark 610 displayed on the second fundus image 520 is moved as appropriate through operation of the control unit 82. Alternatively, the mark 610 may be moved as appropriate using a cursor displayed on the monitor 85 that defines a designation device and is moved by an input device such as a mouse. The control unit 80 obtains a scan condition of the scanning unit 20 that corresponds to a movement position of the mark 610 displayed on the second fundus image 520. Based on the obtained scan condition, the control unit 80 drives the scanning unit 20, and controls the monitor 85 to display a first fundus image 530*a* that corresponds to the mark 610 after moved as shown in FIG. 6B.

In this manner, using the fundus image with the wide view angle when obtaining the fundus image at higher resolution (first fundus image) allows for an easier grasp of the photographed portion of the fundus image at higher resolution.

In the preferred embodiment of the present invention, the liquid-crystal spatial phase modulator is used as the wavefront compensating device; however, the present invention is not limited hereto. It is essential only that the device should be a reflective wavefront compensating device. For example, a deformable mirror that is a form of MEMS (Micro Electro Mechanical Systems) may be used. Having a configuration to mechanically drive a plurality of micromirrors and compensate wavefront aberration of the entering light, the deformable mirror described above is not susceptible to a polarization property of the entering light. The use of the deformable mirror can minimize the amount of the entering light from the light source. Described above is the case of using the reflective wavefront compensating device; however, the present invention is not limited hereto. A transmissive wavefront compensating device may be used, which is arranged to transmit the reflection light from the fundus and compensate wavefront aberration thereof.

In the preferred embodiment of the present invention, the light source arranged to emit the illumination light having the wavelength different from the first light source is used as the light source for aberration detection; however, the present invention is not limited hereto. It is essential only that the light source for aberration detection should have a configuration such that the reflection light from the fundus can be modulated by the wave front compensating device, and the wavefront aberration of the reflection light can be detected by the wavefront sensor. For example, the first light source may be used as the light source for aberration detection.

In the preferred embodiment of the present invention, the wavefront sensor and the wavefront compensating device are made coaxial with the pupil of the examinee's eye; however, the present invention is not limited hereto. It is essential only that the wavefront sensor and the wavefront compensating device should be arranged to detect the wavefront aberration of the examinee's eye and compensate the wavefront aberration. The wavefront sensor and the wavefront compensating device may be made coaxial with the cornea.

In the preferred embodiment of the present invention, the tracking is performed by detecting the positional deviation with the use of the tracking unit having the optical system different from the first and second photographing units; however, the present invention is not limited hereto. It is essential only that ocular movement of the fundus should be detected. The optical systems of the first and second photographing units may be used, and tracking (or, detection of the movement position) with the use of the second photographing unit may be performed.

In the preferred embodiment of the present invention, the movement position of the fundus is detected with the use of the tracking unit, and the first fundus image is displayed following the movement of the fundus; however, the present invention is not limited hereto. If the fundus image is obtained as a still image for fundus observation, the tracking unit is unnecessary.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. A fundus photographing apparatus for photographing a fundus of an examinee's eye, the apparatus comprising:
   a first photographing unit arranged to obtain a first fundus image, the first photographing unit comprising:
   a first illumination optical system arranged to project illumination light to the fundus, the first illumination optical system comprising:

a first light source arranged to emit the illumination light; and a scanning unit arranged to two-dimensionally scan the illumination light on the fundus, the scanning unit comprising:
   a first scanning unit arranged to set a scanning area to scan the illumination light on the fundus; and
   a second scanning unit arranged to move the scanning area, which is set by the first scanning unit, on the fundus;

a first photographing optical system comprising a first photo-receiving element arranged to photo-receive the illumination light reflected from the fundus and obtain the first fundus image; and a wavefront compensating unit comprising:
   a wavefront sensor arranged to photo-receive light reflected from the eye and detect wavefront aberration of the eye; and
   a wavefront compensating device disposed on an optical path of the first photographing optical system and arranged to compensate the wavefront aberration based on a detection result by the wavefront sensor;

a second photographing unit arranged to obtain a second fundus image of a wide area that includes a scanning area by the scanning unit of the first illumination optical system, the second photographing unit comprising:
   a second illumination optical system comprising a second light source arranged to emit illumination light, and arranged to project the illumination light to the fundus; and
   a second photographing optical system comprising a second photo-receiving element arranged to photo-receive the illumination light reflected from the fundus and obtain the second fundus image with a view angle wider than the first fundus image under magnification lower than the first fundus image;

a monitor;

a display control unit arranged to display on the monitor the first fundus image and the second fundus image in a comparable manner, and display an indicator in a superimposing manner on the second fundus image displayed on the monitor, the indicator indicating a photographed portion of the first fundus image; and a unit arranged to move the position of the indicator displayed on the monitor;

wherein the display control unit drives and controls the scanning unit based on information on the position of the indicator displayed on the monitor that is moved by the unit.

2. The fundus photographing apparatus according to claim 1, further comprising:
   a position detecting unit arranged to obtain information on a movement position of the fundus by photographing a predetermined portion of the fundus and detecting a time-varying positional deviation of the portion; and
   a deflecting unit disposed closer to the eye than the scanning unit on the optical path of the first illumination optical system, and arranged to deflect the illumination light via the scanning unit by a predetermined angle,
   wherein the control unit is arranged to drive the deflecting unit based on the movement position information obtained by the position detecting unit.

3. The fundus photographing apparatus according to claim 2, wherein the control unit is arranged to change a position of the indicator displayed on the monitor based on the movement position information.

4. The fundus photographing apparatus according to claim 1, wherein the first photographing unit further comprises a third light source arranged to emit light with a wavelength that is different from a wavelength of the light emitted from the first light source, and the light from the third light source is usable by the wavefront compensating unit.

5. The fundus photographing apparatus according to claim 4, wherein the wavefront compensating unit further comprises:
   a first polarizing unit arranged to polarize the light emitted from the third light source and projected to the fundus such that the light has a given polarization direction; and
   a second polarizing unit arranged to cut off the light having the given polarization direction, and direct light having a polarization direction perpendicular to the given polarization direction to the wavefront sensor, and
   the wavefront compensating device is a liquid-crystal spatial phase modulator, and is disposed so as to compensate wavefront aberration of the light having the polarization direction perpendicular to the given polarization direction.

6. The fundus photographing apparatus according to claim 1, wherein the control unit is arranged to control the emission of the illumination light from the first light source based on a compensation result of the wavefront aberration detected by the wavefront sensor.

7. The fundus photographing apparatus according to claim 1, wherein the control unit is arranged to control the emission of the illumination light from the first light source based on alignment information on the second fundus image obtained by the second photographing unit.

* * * * *